United States Patent [19]

Horwell

[11] Patent Number: 4,738,981

[45] Date of Patent: Apr. 19, 1988

[54] SUBSTITUTED TRANS-1,2-DIAMINOCYCLOHEXYL AMIDE COMPOUNDS

[75] Inventor: David Horwell, Foxton, England

[73] Assignee: Warner-Lambert, Morris Plains, N.J.

[21] Appl. No.: 929,039

[22] Filed: Nov. 10, 1986

Related U.S. Application Data

[62] Division of Ser. No. 669,922, Nov. 13, 1984, Pat. No. 4,656,182.

[51] Int. Cl.$^4$ .................. A61K 31/40; A61K 31/34; C07D 405/08; C07D 307/81
[52] U.S. Cl. .................. 514/422; 514/469; 548/525; 549/470; 549/60
[58] Field of Search .................. 548/525; 549/470, 60; 514/469, 422, 444

[56] References Cited

U.S. PATENT DOCUMENTS 4,145,435  3/1979  Szmuszkovicz ............... 514/210 X
4,359,476  11/1982  Kaplan et al. ...................... 514/409

Primary Examiner—Donald G. Daus
Assistant Examiner—William A. Teoli, Jr.
Attorney, Agent, or Firm—Jerry F. Janssen

[57] ABSTRACT

Substituted trans-1,2-diaminocyclohexyl amide compounds demonstrating selective opioid receptor binding possess utility as analgesic, diuretic, and psychotherapeutic agents. A method of preparing the compounds, pharmaceutical compositions employing the compounds, and a method of alleviating pain employing the compounds are also disclosed.

5 Claims, No Drawings

SUBSTITUTED TRANS-1,2-DIAMINOCYCLOHEXYL AMIDE COMPOUNDS

CROSS-REFERENCE TO RELATED APPLICATIONS

This application is a divisional application of copending application Ser. No. 669,922, filed 11/13/84 now U.S. Pat. No. 4,656,182.

BACKGROUND OF THE INVENTION

The search for strong analgesics which also possess minimal potential for dependency has been among the highest priority efforts in pharmacological research. These research efforts have, to a great extent, involved chemical modifications of the opiate structure and the discovery of chemically novel compounds which possess morphine-like activity.

The discovery of endogenous opioids had led workers in the field to consider that these peptides, possessing less rigid structures, might interact with opioid receptors other than those to which the classical rigid structure opiates, such as morphine, bind.

The concept of multiple opioid receptors has been supported by studies with nalorphine and a series of benzomorphans which display unusual pharmacological properties dissimilar from morphine, yet blocked by the selective opioid antagonists. [See, for example, W. R. Martin, et al., *J. Pharmacol. Exp. Ther.*, 197: 517–532 (1976)].

The existence of multiple types of opioid receptors is of importance because it suggests the possibility of separating the desirable analgesic and psychotherapeutic effects of a drug compound from the undesirable abuse potential or habituating effects.

U.S. Pat. No. 4,145,435 describes certain 2-aminocycloaliphatic amide compounds as analgesics. In particular, trans-3,4-dichloro-N-methyl-N-[2-(1-pyrrolidinyl)-cyclohexyl]-benzacetamide has been reported to possess selective kappa agonist activity, and therefore to possess analgesic activity without attendant dependence liability. [See P. V. Vanvoigtlander, et al., *J. Pharmacol. Exp. Ther.*, 224: 7–12 (1983)].

Recently, the diuretic effect of various opioid agonists and antagonists has been studied, and it has been shown that kappa agonists tend to increase urination, while mu agonists decreased urination. See J. D. Leander, *J. Pharmacol. Exp. Ther.*, 227: 35–41 (1983)]. These findings suggest that selective opioid agonists and antagonists also possess potential as diuretics.

SUMMARY OF THE INVENTION

The present invention relates to substituted trans-1,2-diamino-cyclohexylamide compounds useful as analgesics, diuretics, and psychoterapeutic agents. The invention is also concerned with a method of preparing such compounds, pharmaceutical compositions including such compounds, and with a method of alleviating pain in a mammal by administering an effective amount of a pharmaceutical composition in accordance with the present invention.

It its broadest aspect, the present invention encompasses compounds having structural formula I

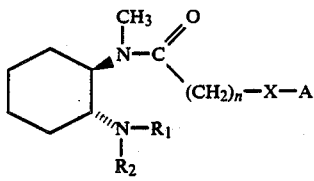

where $R_1$ is methyl and $R_2$ is hydrogen, alkyl of from one to six carbon atoms,

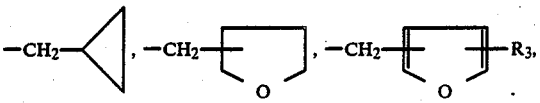

—$CH_2CH$=$CR_3R_4$ where $R_3$ and $R_4$ are independently hydrogen or methyl; or where $R_1$ and $R_2$ taken together with the nitrogen atom to which they are attached form a ring denoted by

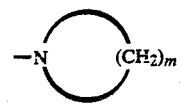

where m is an integer of from three to eight; where n is an integer of from zero to six; X is oxygen, sulfur, or $CHR_5$, where $R_5$ is hydrogen, alkyl of from one to six carbon atoms, or aryl; $NR_6$ where $R_6$ is hydrogen or alkyl of from one to six carbon atoms; where A is

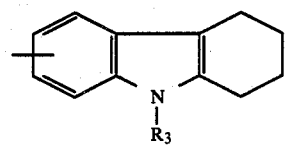

or

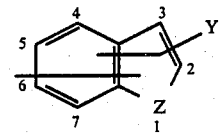

where Y is hydrogen, fluorine, chlorine, alkyl of from one to six carbon atoms, or aryl; and X is oxygen, sulfur, —$CH_2$—, or $NR_7$ where $R_7$ is hydrogen, alkyl of from one to six carbon atoms or, when X is $CHR_5$, $R_7$ is a direct bond to X; or $N^1$-oxides thereof; and the pharmaceutically acceptable acid addition salts thereof.

In structural formula IIIB for subunit "A" above, the bond shown attaching the group "Y" to the fused ring system is drawn to intersect both rings of the fused ring system. This notation is meant to indicate that Y may be attached to the fused ring system at positions 2, 3, 4, 5, 6, and 7.

Likewise, the position of attachment of the group designated "X" to the fused ring system designated "A" may be at positions 2, 3, 4, 5, 6, or 7. Moreover, when Z is a nitrogen atom and X is $CHR_5$, the nitrogen atom of the heterocyclic fused ring system may be attached by a direct bond to X.

Also contemplated as falling within this aspect of the present invention are the $N^1$-oxides of compounds having structural formula I above. The meaning of the term "N¹-oxides" is made clear by referring to structural formula Ia below in which the nitrogen atoms have been numbered. The alkyl-substituted nitrogen atoms is numbered "1" and the amido-nitrogen atom is numbered "2." In those cases where Z is also nitrogen, this is numbered nitrogen atom "3."

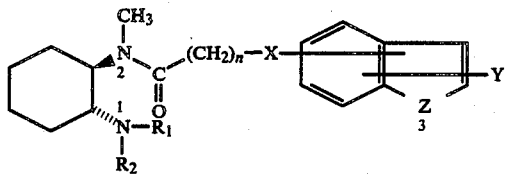

Oxidation of compounds of structural formula I above with, for example, m-chloroperbenzoic acid or other suitable oxidizing agents, readily converts the more basic alkyl-substituted nitrogen atom attached to the cyclohexane ring to its corresponding N-oxide. Throughout this specification and the appended claims, the term "N¹-oxide" is meant to refer to these compounds.

In accordance with a second aspect of the present invention, a method of preparing compounds having structural formula I comprises reacting a substituted trans-cyclohexyldiamine of structure II

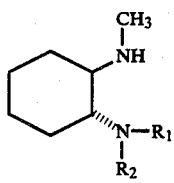

with a substituted carboxylic acid of structural formula III.

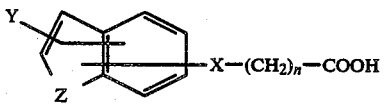

In accordance with another aspect of the present invention, pharmaceutical compositions useful for the alleviation of pain in a mammal comprise an effective amount of a compound having structural formula I above, in combination with a pharmaceutically acceptable carrier.

In a further aspect of the present invention, a method of alleviating pain in a mammal comprises administering to a mammal suffering from pain an effective amount of a pharmaceutical composition, preferably in unit dosage form, which composition includes a compound having structural formula I, above, in combination with a pharmaceutically acceptable carrier.

DETAILED DESCRIPTION

Compounds of the present invention comprise a class of derivatives of trans-1,2-diaminocyclohexane in which one nitrogen is a tertiary amine nitrogen substituted with methyl and a substituent selected from the group R₂ as defined above or, preferably is a tertiary amine nitrogen attached to the cyclohexane ring and which preferably is part of a pyrrolidinyl, piperidinyl or homopiperidinyl group. The other nitrogen atom of the 1,2-diaminocyclohexane is an N-methyl amide nitrogen.

In the formula for the subunit designated "A" above, the bonds shown attaching the groups "X" and "Y" to the fused ring system are drawn to intersect both the carbocyclic and the heterocyclic rings of the fused ring system. This rotation is meant to indicate that X and Y may be attached to the fused ring system at positions 2, 3, 4, 5, 6, or 7. Moreover, when Z is nitrogen, X may be attached to position 1. In those cases where Y is hydrogen, alkyl, or aryl, Y may likewise be attached to position 1 when X is attached at a position 2 through 7.

By the term "alkyl of from one to six carbon atoms" as used throughout this specification and the appended claims is meant branched or unbranched saturated hydrocarbon groupings containing one to six carbon atoms. Examples include methyl, ethyl, n-propyl, iso-propyl, n-butyl, sec-butyl, iso-butyl, n-pentyl, and the like.

By the term "aryl" is meant phenyl; phenyl substituted with fluorine, chlorine, alkyl of from one to six carbon atoms, alkoxy of from one to six carbon atoms, nitro, and trifluoromethyl; thienyl; and thienyl substituted with alkyl of from one to six carbon atoms, and alkoxy of from one to six carbon atoms.

By the term "alkoxy" is meant a branched or unbranched hydrocarbon grouping such as "alkyl" as defined above, attached to an oxygen atom.

By the term "acyl" as used herein is meant an organic radical derived from an organic acid by the removal of the hydroxy group, for example, acetyl, benzoyl, methanesulfonyl, benzenesulfonyl, p-toluenesulfonyl and the like. Thus, the term is meant to encompass alkanoyl and alkanesulfonyl where the alkyl portion is "alkyl" as defined above; aroyl and arylsulfonyl where the aromatic portion if "aryl" as defined above.

Compounds of the present invention may contain one or more asymmetric carbon atoms and thus exist as enantiomers or diastereomers. The present invention contemplates all possible optical isomeric forms of structural formula I given above. Individual enantiomorphic or diastereomeric forms of the compounds of this invention may be obtained from mixtures by known methods of resolution.

In a preferred embodiment, compounds of formula I are those wherein Y is hydrogen.

In another preferred embodiment, compounds of formula I are those wherein n is zero and X is —CHR₅ where R₅ is as defined above.

In yet another preferred embodiment, compounds of formula I are those wherein Y is sulfur or =NR₇ where R₇ is as defined above.

Examples of compounds contamplated as falling within the scope of the present invention are the following:

trans-N,2-dimethyl-N-[2-(1-pyrrolidinyl)cyclohexyl]-3-benzofuranacetamide;
trans-N-methyl-3-phenyl-N-[2-(1-pyrrolidinyl)cyclohexyl]-5-benzofuranacetamide;
trans-N-methyl-N-[2-(1-pyrrolidinyl)cyclohexyl]-benzo[b]thiophene-4-acetamide;
trans-N-methyl-N-[2-(1-pyrrolidinyl)cyclohexyl]-benzo[b]thiophene-3-acetamide;
trans-N-methyl-N-[2-(methylamino)cyclohexyl]-benzo[b]thiophene-4-acetamide;
trans-N-methyl-N-[2-[methyl(2-propenyl)amino]-cyclohexyl]benzo[b]thiophene-4-acetamide;

trans-N-[2-[(cyclopropylmethyl)methylamino]-cyclohexyl]-N-methylbenzo[b]thiophene-4-acetamide;

trans-N-methyl-N-[2-[methyl(2-propynyl)amino]-cyclohexyl]-benzo[b]thiophene-4-acetamide;

trans-N-methyl-7-propyl-N-[2-(1-pyrrolidinyl)-cyclohexyl]-benzo[b]thiophene-4-acetamide;

trans-N-methyl-N-[2-(1-pyrrolidinyl)cyclohexyl]3-(2-thienyl)benzo[b]thiophene-7-acetamide;

trans-N-methyl-3-phenyl-N-[2-(1-pyrrolidinyl)-cyclohexyl]benzo[b]thiophene-5-acetamide;

trans-N-methyl-N-[2-(1-piperidinyl)cyclohexyl]-benzo[b]thiophene-4-acetamide;

trans-N-methyl-N-[2-[methyl[(tetrahydro-2-furanyl)-methyl]amino]cyclohexyl]benzo[b]thiophene-4-acetamide;

trans-N-methyl-N-[2-methyl(3-methyl-2-butenyl)-amino]cyclohexyl]benzo[b]thiophene-4-acetamide;

trans-N-[2-[(1,1-dimethyl-2-propenyl)methylamino]-cyclohexyl]-N-methylbenzo[b]thiophene-4-acetamide;

trans-N,5-dimethyl-N-[2-(1-pyrrolidinyl)cyclohexyl]-benzo[b]thiophene-3-acetamide;

trans-5-chloro-N-methyl-N-[2-(1-pyrrolidinyl)-cyclohexyl]benzo[b]thiophene-3-acetamide;

trans-N-methyl-N-(2-pyrrolidinylcyclohexyl)-4-benzo[b]thiophene-2-propionamide;

trans-2-(benzo[b]thiophen-3-yloxy)-N-methyl-N-[2-(1-pyrrolidinyl)cyclohexyl]acetamide;

trans-N-methyl-N-[2-(1-pyrrolidinyl)cyclohexyl]-1H-indene-3-acetamide;

trans-N-methyl-N-[2-(1-pyrrolidinyl)cyclohexyl]-1H-indene-2-acetamide;

trans-N-methyl-N-[2-(1-pyrrolidinyl)cyclohexyl]-1H-indole-3-acetamide;

trans-N-methyl-N-[2-(1-pyrrolidinyl)cyclohexyll]-1H-indole-3-propanamide;

trans-N-methyl-N-[2-(1-pyrrolidinyl)cyclohexyl]-1H-indole-3-butanamide;

trans-N-methyl-N-[2-(1-pyrrolidinyl)cyclohexyl]-1H-indole-1-acetamide;

trans-N-[2-(1-pyrrolidinyl)cyclohexyl]-N,2,3-trimethyl-1H-indole-5-acetamide;

trans-2,3,4,9-tetrahydro-N,9-dimethyl-N-[2-(1-pyrrolidinyl)cyclohexyl]-1H-carbazole-6-acetamide.

In general, compounds of the present invention are prepared by reacting the appropriate trans-1,2-diaminocyclohexane of structural formula II

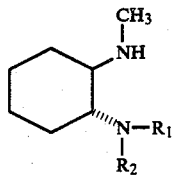
II with a carboxylic acid of structural formula II

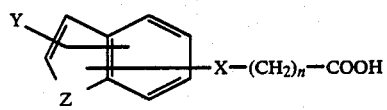
III or a reactive derivative formed from such a carboxylic acid.

The appropriate carboxylic acid (III) may be reacted directly with the amine with the aid of such reagents as dicyclohexylcarbodiimide and the like. Alternatively, the carboxylic acids are first converted to a reactive derivative such as an activated ester, anhydride, acid halide such as the bromide or chloride, or acyl imidazoles of the formula IV

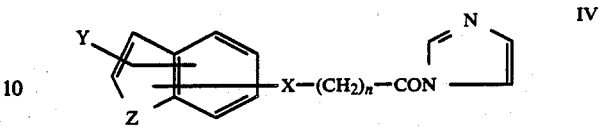
IV and the resulting carboxylic acid derivative reacted with the substituted trans-1,2-diaminocyclohexane (II).

For example, the reaction between the cyclic diamine (II) and the appropriate carboxylic acid (III) is carried out in the presence of the coupling reagent, dicyclohexylcarbodiimide, in a cyclic ether solvent such as tetrahydrofuran or dioxane until the desired product is formed. The reaction will generally proceed at ambient temperatures but, depending upon the reactivity of the specific materials involved, the desired reaction time, the solvent being employed, and the molar proportions of reagents, the reaction temperature may be varied between about $-25°$ C. and the reflux temperature of the solvent employed.

The reaction between the acid halide and the cyclic diamine (II) is carried out, generally at ambient temperature, in a suitable solvent in the presence of an acid acceptor such as a tertiary amine or an alkali metal or alkaline earth metal carbonate or bicarbonate. The mixture of the amine and the acid halide is allowed to stand until reaction is complete.

When the reaction between the cyclic diamine (II) and the acid (III) or acid derivative has proceeded to substantial completion, the desired product is recovered from the reaction mixture by techniques well known to practitioners of the organic chemical arts.

For example, the reaction mixture can be evaporated under vacuum, if desired, to remove the solvent and other volatile components of the reaction mixture to yield the product, generally as an oil. This residual material is then taken up in a solvent such as diethyl ether, washed first with a salt solution such as sodium bicarbonate solution and then with water. Separation of the organic phase, drying over, for example anhydrous magnesium sulfate, and evaporation of the ether solvent, yields the desired product, usually as an oil or crystalline solid.

The starting trans-1,2-diaminocyclohexane compounds of the present invention are prepared by the method detailed in U.S. Pat. No. 4,145,435. The carboxylic acids (III) are known, or if novel, are prepared by reaction sequences well known in the art. The acyl imidazole derivatives (IV) of the carboxylic acids are prepared by reacting carbonyldiimidazole with the appropriate acid.

The free base form of the compounds of this invention are readily converted, if desired, by known methods to the acid addition salts by reaction with any of a number of inorganic or organic acids including hydrochloric, hydrobromic, hydriodic, sulfuric, nitric, phosphoric, acetic, benzoic, citric, maleic, tartaric, succinic, gluconic, ascorbic, sulphamic, oxalic, pamoic, methanesulfonic, benzenesulfonic, and related acids and mixtures thereof. The free base form of the compounds of the present invention and the acid addition salt may differ in certain of their physical properties, such as solubility in polar solvents, but are otherwise equivalent for the purposes of this invention.

The compounds of the present invention possess significant analgesic activity with potential for minimum dependence liability due to their selective kappa opioid receptor binding properties. In addition to analgesics, selective kappa agonists also cause opioid receptor-mediated sedation, diuresis, and corticosteroid elevations. Accordingly, the compounds of the present invention may also be useful diuretics and psychotherapeutic agents as well as analgesics.

Representative examples of the compounds of formula I have shown positive activity in standard laboratory analgesic tests such as writhing and hot plate with animals such as mice. For example, compounds of Examples 1 and 2 when given at 10 mg/kg s.c. (subcutaneous administration) of animal body weight, caused abolition of writhing in the acetylcholine-induced writhing test. When compared with control, mice also showed longer tolerance of heat on a hot plate at 55° C. when given 10 mg/kg s.c. of the compound of Example 1.

Representative examples of the compounds of the present invention, when tested in vitro to determine the extent of opioid receptor binding, were found to be selectively bound to the kappa receptors with evidence of little or no binding to the mu and delta receptors. The benefits of this selective binding has already been mentioned above and is also described by M. B. Tyers, Br. J. Pharmac (1980) 69:503–512.

Measurement of the kappa opioid receptor site binding activity of compounds of the present invention was made by the following method. Guinea pig brain homogenates were prepared fresh each day utilizing the method of Gillan, et al, Br. J. Pharm., 70:481–490 (1980).

The binding of tritiated etorphine to brain homogenates was measured in the presence of unlabelled competitor compounds of the present invention with 200 nanomolar D-Ala-D-Leu-enkephalin (acronym DADLE) and 200 nanomolar D-Ala-MePheBly-ol-enkephalin (acronym DAGO) added to saturate the delta and mu opioid receptors, respectively. The reaction was terminated by rapid filtraton and the radioactivity bound to the filters counted by liquid scintillation spectrophotometry.

Measurement of the mu and delta opioid receptor site binding activity of compounds of the present invention was made by the following method. Guinea pig homogenates were prepared fresh each day utilizing the method of Gillan, et al, cited above.

Homogenates were incubated for 150 minutes at 0° C. with either tritiated DAGO to measure mu receptor site binding activity, or with tritiated DADLE in the presence of a ten-fold excess of unlabelled DAGO to measure delta opioid receptor site activity. Nonspecific binding was determined in the presence of $10^{-6}$M DAGO and $10^{-6}$M DADLE.

Reactions were terminated by rapid filtration and the radioactivity bound to the filters counted by liquid scintillation spectrophotometry.

Data was analyzed by the methods of Scatchard, Ann. N.Y. Acad. Sci., 51:660–672 (1949) and Hill, J. Physiol., 40:IV–VIII (1910). The inhibition of binding of tritriated etorphine, DAGO and DADLE by cold ligands was determined from the regression of log percentage inhibition of specific binding or log concentration of cold ligand. The inhibition constant ($K_i$) was calculated from the equation:

$$K_i = \frac{IC_{50}}{1 + [L]/K_D}$$

where [L] is the concentration of the labelled ligand and $K_D$, its equilibrium dissociation constant.

The results of these tests for several representative compounds of the present invention are presented in Table I.

TABLE 1

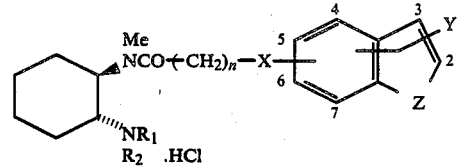

| $R_1$ $R_2$ | n | x | z | y | (Ki M) Kappa | Mu |
|---|---|---|---|---|---|---|
| c-C$_4$H$_8$ | 0 | 4-CH$_2$ | S | H | 3.73 × 10$^{-9}$ | 4.08 × 10$^{-7}$ |
| c-C$_4$H$_8$ | 0 | 5-CH$_2$ | NCH$_3$ | 2,3-cC$_4$H$_8$ | 3.97 × 10$^{-6}$ | 4.67 × 10$^{-7}$ |
| c-C$_4$H$_8$ | 0 | 3-CH$_2$ | NH | H | 7.45 × 10$^{-8}$ | 2.94 × 10$^{-6}$ |
| c-C$_4$H$_8$ | 0 | 3-CH$_2$ | S | H | 4.85 × 10$^{-8}$ | >10$^{-6}$ |
| CH$_3$, H | 0 | 4-CH$_2$ | S | H | 10$^{-6}$–10$^{-7}$ | >10$^{-6}$ |
| c-C$_4$H$_8$ | 1 | 3-CH$_2$ | NH | H | >>10$^{-6}$ | >>10$^{-6}$ |
| CH$_3$, CH$_2$—cC$_3$H$_4$ | 0 | 4-CH$_2$ | S | H | ~10$^{-7}$ | 10$^{-6}$–10$^{-7}$ |
| CH$_3$, CH$_2$CH:CH$_2$ | 0 | 4-CH$_2$ | S | H | ~10$^{-7}$ | 2.1 × 10$^{-7}$ |
| c-C$_4$H$_8$ | 2 | 3-CH$_3$ | NH | H | >10$^{-6}$ | NT |
| c-C$_4$H$_8$ | 0 | 3-CH$_2$ | O | 2-CH$_3$ | 7.89 × 10$^{-8}$ | ~10$^{-5}$ |
| c-C$_4$H$_8$ | 0 | 3-CH$_2$ | CH$_2$ | H | ~10$^{-7}$ | ~10$^{-5}$ |
| c-C$_4$H$_8$ | 0 | 5-CH$_2$ | O | 3-Ph | ~10$^{-6}$ | ~10$^{-5}$ |
| c-C$_4$H$_8$ | 0 | 2-CH$_2$ | CH$_2$ | H | ~10$^{-5}$ | ~10$^{-5}$–10$^{-6}$ |
| c-C$_4$H$_8$ | 0 | 7-CH$_2$ | S | 3-(2'-thiophene) | ~10$^{-5}$ | NT |
| c-C$_4$H$_8$ | 0 | 5-CH$_2$ | S | 3-Ph | ~10$^{-5}$ | NT |
| c-C$_4$H$_8$ | 0 | 4-CH$_2$ | S | 7-nPr | 4.24 × 10$^{-8}$ | 1.82 × 10$^{-7}$ |
| c-C$_5$H$_{10}$ | 0 | 4-CH$_2$ | S | H | 2.45 × 10$^{-7}$ | 2.41 × 10$^{-6}$ |
| CH$_3$—2-tetrahydrofurfuryl | 0 | 4-CH$_2$ | S | H | 10$^{-6}$–10$^{-7}$ | NT |
| c-C$_4$H$_8$ | 0 | 4-CHMe | S | H | >10$^{-6}$ | NT |
| CH$_3$, CH$_2$CH:CMe$_2$ | 0 | 4-CH$_2$ | S | H | 2.05 × 10$^{-7}$ | 3.25 × 10$^{-8}$ |

The compounds of the present invention, and/or the nontoxic, pharmaceutically acceptable salts thereof, may be administered to mammals in pharmaceutical compositions or formulations which comprise one or more of the compounds of this invention and/or the nontoxic, pharmaceutically acceptable, nontoxic carrier.

The compounds of this invention may be administered parenterally in combination with conventional injectable liquid carriers such as sterile pyrogen-free water, sterile peroxide-free ethyl oleate, dehydrated alcohols, propylene glycol, and mixtures thereof.

Suitable pharmaceutical adjuvants for the injecting solutions include stabilizing agents, solubilizing agents, buffers, and viscosity regulators. Examples of these adjuvants include ethanol, ethylenediamine tetraacetic acid (EDTA), tartrate buffers, citrate buffers, and high molecular weight polyethylen oxide viscosity regulators. These pharmaceutical formulations may be injected intramuscularly, intraperitoneally, or intravenously.

Compounds of the present invention, and/or the nontoxic, pharmaceutically acceptable salts thereof, may be administered to mammals orally in combination with conventionally compatible carriers in solid or in liquid form. These oral pharmaceutical compositions may contain conventional ingredients such as binding agents selected form the group consisting of syrups, acacia, gelatin, sorbitol, tragacanth, polyvinylpyrrolidone, and mixtures thereof. The compositions may further include fillers such as lactose, mannitols, starch, calcium phosphate, sorbitol, methylcellulose, and mixtures thereof.

These oral compositions may also contain lubricants such as magnesium stearate, high molecular weight polymers such as polyethylene glycol, high molecular weight fatty acids such as stearic acid silica, or agents to facilitate disintegration of the solid formulation, such as starch, and wetting agents such as sodium lauryl sulfate.

The oral pharmaceutical compositions may take any convenient form such as tablets, capsule, lozenges, aqueous or oily suspensions, emulsions, or even dry powders which may be reconstituted with water and/or other liquid media prior to use.

Compounds of the present invention and/or the nontoxic, pharmaceutically acceptable salts thereof may be administered topically in the form of an ointment or cream containing from about 0.1% to 10% by weight of the actie component in a pharmaceutical ointment or cream base.

Compounds of the present invention and/or the nontoxic, pharmaceutically acceptable salts thereof, may be administered to mammals rectally in the form of suppositories. For preparing suppositories, a low-melting wax such as a mixture of fatty acid glycerides or cocoa butter is first melted, and the active ingredient is dispersed homogeneously therein by stirring. The molten homogeneous mixture is then poured into convenient sized molds, allowed to cool and thereby solidify.

The solid or liquid forms may contain flavorants, sweeteners, and/or preservatives such as alkyl p-hydroxybenzoates. The liquid forms may further contain suspending agents such as sorbitol, glucose, or other sugar syrups, methyl-, hydroxymethyl-, or carboxymethylcellulose, and gelatin, emulsifying agents such as lecithin or sorbitol monooleate, and conventional thickening agents. The liquid compositions may optionally be encapsulted in, for example, gelatin capsules, in an effective amount.

Preferably, the pharmaceutical compositions of this invention are in unit dosages form. In such form, the preparation is subdivided into unit doses containing apropriate amounts of the active component. The unit doses form can be a packaged preparation with the package containing discrete quantities of the preparation. For example, the package may take the form of packeted tablets, capsules, and powders in envelopes, vials or ampoules. The unit dosage form can also be a capsule, cachet, or tablet itself or can be the appropriate number of any of these packaged forms. The quantity of active compound in a unit dose of preparation may be varied or adjusted from 0.5 mg to about 350 mg according to the particular application and the potency of the active ingredient.

When employed systematically in therapeutic use as analgesic agents in the pharmaceutical method of this invention, the compounds are administered at doses of about 0.05 mg to 2.0 mg of active compound per kilogram of body weight of the recipient.

General synthetic methods for preparing compounds of the present invention wherein $R_1$ and $R_2$, taken together, form a pyrrolidinyl ring are given below in Methods A–D. Examples 1–30 illustrate the preparation of particular compounds in accordance with the present invention.

GENERAL SYNTHETIC METHODS

Preparation of amide monohydrochlorides (2 mmol scale)

Method A: Trans-N-methyl-2-(1-pyrrolidinyl) cyclohexanamine (364 mg, 2 mmol) in methylene chloride (5 ml) was added with stirring to a solution of the acid chloride [prepared by the action of thionyl chloride (5 ml) on the appropriate carboxylic acid (2 mmol)] in methylene chloride (20 ml). After stirring for ten minutes, the mixture was evaporated to small volume and diethyl ether added until no more precipitate appeared. The product was collected by filtration, washed with diethyl ether, and dried in a vacuum oven at 70° C. overnight.

Method B: Trans-N-methyl-2-(1-pyrrolidinyl)-cyclohexanamine (364 mg, 2 mmol) in methylene chloride (5 ml) was added with stirring to a solution of the acid chloride [prepared by the action of thionyl chloride (5 ml) on the appropriate carboxylic acid (2 mmol)] in a 1:1 mixture of methylene chloride and diethyl ether (20 ml). After stirring for ten minutes, diethyl ether was added until no more precipitate appeared. The product was collected by filtration, washed with diethyl ether, and dried in a vacuum oven at 70° C. overnight.

Method C: A solution of carbonyl di-imidazole (356 mg, 2.2 mmol) in dry tetrahydrofuran (10 ml) was added to a solution of the appropriate carboxylic acid (2 mmol) in tetrahydrofuran (20 ml). The mixture was stirred for 30 minutes at room temperature. Trans-N-methyl-2-(1-pyrrolidinyl)cyclohexanamine (364 mg, 2 mmol) in tetrahydrofuran (10 ml) was added, the mixture heated to reflux, then stirred at room temperature for 16 hours. The reaction was evaporated to small volume, and the residue dissolved in ethyl acetate (100 ml). The extract was washed with saturated sodium bicarbonate (3×50 ml), then water (50 ml), dried (MgSO$_4$), and evaporated under reduced pressure.

Method D: Substantially as described in Method C with the exception that the mixture of reactants was stirred at ambient temperature for 16 hours rather than being heated under reflux.

The following examples are provided to enable one skilled in the art to practice the present invention. The examples are not to be read as limiting the scope of the invention as defined by the appended claims, but as merely illustrative thereof.

EXAMPLE 1

Preparation of trans-N-methyl-N-[2-(1-pyrrolidinyl)-cyclohexyl]benzo[b]thiophene-4-acetamide A. Preparation of 7-methyl-7-azabicyclo[4.1.0]heptane [Modification of method of T. Taguchi and M. Eto, *J. Amer. Chem. Soc.* 80, 4076 (1958)].

i. Cyclohexene oxide (Aldrich, 196.3 g 2M) was added to a 25/30% solution of aqueous methylamine (745 ml, 6M) (25% solution) dropwise with stirring and cooling in an icebath over one hour, during which time the temperature reached 46° C. The solution was stirred at room temperature overnight, and then refluxed for three hours in fume hood. The solution was cooled in an icebath and saturated with solid NaOH, extracted with 4×200 ml ether, dried (MgSO$_4$) and evaporated to dryness on rotary evaporator.

The crude product, trans-2-(methylamino)-cyclohexanol, was distilled under water vacuum pressure, the first small sample of cyclohexene epoxide discarded. The bulk was distilled from a 1-liter flask with a 60 W isomantile and a short Leibig condenser over a two hour period to yield the product.

bp: 118° C. (water vacuum).

yield: 208 g (81%).

ii. Trans-2(methylamino)cyclohexanol (208 g, 1.61M) was placed in a three liter beaker and dissolved in ether (400 ml). Chlorosulphonic acid (1.89 g, 1.62M) was added dropwise to the ice-salt cooled solution. Added a further 200 ml of ether. The solution was hand stirred. Addition took one hour. The solution/solid was allowed to warm to room temperature and stand for three hours. The ether was decanted and the white salt washed with 300 ml ether which was also decanted.

The solid was cooled in ice-salt bath and NaOH (218 g in one liter water) added slowly. The thick white solid was left at room temperature overnight.

The crude product, 7-methyl-7-azabicyclo [4.1.0] heptane, was distilled in isomantle with continuous addition of water from separating funnel to retain approximately original volume. After 600 ml of liquid had been collected, the total distillate was saturated with solid NaOH, extracted with 5×200 ml ether, dried (MgSO$_4$) and evaporated on rotary evaporator.

The product was distilled using a water vacuum and air bleed, the collection vessel being cooled in an ice bath.

yield: 67 g (37%), b.p. 38° C. (water vacuum and bleed).

iii. Preparation of trans-N-Methyl-2-(1-pyrrolidinyl)-cyclohexyanamine.

A mixture of 7-Methyl-7-azabicyclo[4.1.0]heptane (7.0 g, 0.063M), pyrrolidine (17.92 g, 0.25M), water (10 ml) and ammonium chloride (0.16 g) was stirred and refluxed for 21 hours. The solution was cooled and solid sodium hydroxide added and extracted with ether (3×50 ml). The extracts were dried over magnesium sulphate and evaporated under reduced pressure to a brown oil. This was distilled under high vacuum to yield a colorless oil.

bp: 95° C. (6.0 g).

B. Preparation of trans-N-methyl-N-[2-(1-pyrrolidinyl)cyclohexyl]benzo[b]thiophene-4-acetamide monohydrochloride.

By Method B, benzo[b]thiophene-4-acetic acid (192 mg, 1 mmol) was converted to the amide monohydrochloride (376 mg, 96%); VmaxC=O 1640 cm$^{-1}$.

EXAMPLE 2

Preparation of trans-N-methyl-N-[2-(1-pyrrolidinyl)-p-cyclohexyl]-1H-indole-3-acetamide monohydrochloride A. Trans-N-methyl-2-(1-pyrrolidinyl)cyclohexanamine was prepared as described in example 1 above.

B. Preparation of trans-N-methyl-N-[2-(1-pyrrolidinyl)cyclohexyl]-1H-indole-3-acetamide monohydrochloride.

Trans-N-methyl-2-(1-pyrrolidinyl)cyclohexanamine (0.368 g) was dissolved in methylene chloride (10 ml) and stirred at room temperature. The acid chloride of 3-indole acetic acid (prepared by the action of thionyl chloride on 3-indole acetic acid, 0.35 g ) dissolved in methylene chloride (10 ml) was added and let stand for five hours. Ether was added to rapidly stirred solution until no more precipitate appeared. After further rapid stirring for one hour, the precipitate was filtered and dried in a vacuum oven at 90° C. for one hour and stored in a predried bottle. The product was in the form of a black glassy solid (300 mg).

EXAMPLE 3

Preparation of trans-N-methyl-N-[2-(1-pyrrolidinyl) cyclohexyl]-1H-indole-3-acetamide free base 1H-Indole 3-acetic acid (1.05 g, Aldrich) and trans-N-methyl-2-(1-pyrrolidinyl)cyclohexanamine were dissolved in tetrahydrofuran (30 ml) and cyclohexyl carbodiimide (1.24 g) added. The resultant solution was stirred at room temperature overnight, during which time a white precipitate appeared.

The solution was filtered and evaporated to an oil, which was chromatographed on silica. Elution with ether gave the product as a white solid (1.3 g), mp 175–178° C.

EXAMPLE 4

Trans-(±)-N-methyl-N-[2-(1-pyrrolidinyl)cyclohexyl]-1H-indole-3-propanamide monohydrochloride By Method C, indole-3-propanoic acid (0.752 g, 4 mmol) was converted to the amide monohydrochloride (0.65 g, 42%) isolated as white crystals, mp 143.5–145° C.

EXAMPLE 5

Trans-(±)-N-methyl-N-[2-(1-pyrrolidinyl)cyclohexyl]-1H-indole-3-butanamide dihydrogen sulphate By Method D, indole-3-butyric acid (406 mg, 2 mmol) was treated with carbonyl diimidazole (356 mg, 2 mmol) and the diamine (364 mh, 2 mmol). After standing for 16 hours at room temperature the mixture was refluxed for a further 20 hours. The crude product was purified by column chromatography (silica gel eluted with CH$_2$CL$_2$:EtOH:0.880 NH$_3$, 18:2:1, lower layer) to give the pure free base. The dihydrogen sulphate salt was then prepared by the addition of an ethereal solution of the amine, giving the product as a very hygroscopic solid (190 mg, 20%); Vmax 1635 cm$^{-1}$.

EXAMPLE 6

Trans-(+)-N-methyl-N-[2-(1-pyrrolidinyl)cyclohexyl]-1H-indole-1-acetamide

Triethylamine (139 μl, 1 mmol) was added to a solution of 1H-indole-1-acetic acid (175 mg, 1 mmol) in tetrahydrofuran (10 ml) at −15° C. with vigorous stirring. Ethyl chloroformate (96 μl, 1 mmol) was added, and the mixture stirred for five minutes. A solution of trans-(±)-N-methyl-2-(1-pyrrolidinyl)-cyclohexanamine (182 mg, 1 mmol) in tetrahydrofuran (2 ml) was added, and stirring continued for 30 minutes at −15° C., then 30 minutes at room temperature. The reaction was evaporated to small volume, the residue dissolved in ethyl acetate (50 ml), and washed with saturated sodium biocarbonate solution (3×50 ml). The organic extract was drige (MgSO$_4$), evaporated under reduced pressure, and recrystallized from diethyl ether/methylene chloride to yield the amide (100 mg, 32%); Vmax C=O 1635 cm$^{-1}$.

EXAMPLE 7

Trans-(±)-N-[2-(1-pyrrolidinyl)cyclohexyl]-N,2,3-trimethyl-1H-indole-5-acetamide Triethylamine (139 μl, 1 mmol) was added to a solution of 2,3-dimethyl-1H-indole-5-acetic acid (203 mg, 1 mmol) in tetrahydrofuran (10 ml) at −15° C., with vigorous stirring. Ethyl chloroformate (96 μl, 1 mmol) was added, and the mixture stirred for five minutes. A solution of trans-(±)-N-mthyl-2-(1-pyrrolidinyl)cyclohexanamine (182 mg, 1 mmol) in tetrahydrofuran (2 ml) was added, and stirring continued for 30 minutes at −15° C., then 30 minutes at room temperature. The reaction was evaporated to small volume, the residue taken into ethyl acetate (50 ml), and washed with saturated sodium bicarbonate solution (3×50 ml). The organic extract was dried (MgSO$_4$), evaporated under reduced pressure and recrystallized from ethyl acetate to yield the amide (204 mg, 56%); VmaxC=O 1615 cm$^{-1}$.

EXAMPLE 8

Trans-(±)-N,N'-dimethylcyclohexane-1,2-diamine

A vigorously stirred mixture of N-methylazabicyclo-[4.1.0]-heptane (36.1 g), monomethylamine (162 ml of a 23–30% aqueous solution) and ammonium chloride (0.50 g) was heated in an oil bath at 94°–99° C. for 21.5 hours. After cooling to 0° C. the mixture was treated with sodium hydroxide (10g) and extracted with diethyl ether (4×100 ml). The combined ethereal fractions furnished a residue which was distilled to give pure trans-(×)-N-N'-dimethylcyclo- hexane-1,2-diamine (18 g, 39%); b.p. 78° C. (14 mm) which solidified after standing at 17° C.; found: C, 67.5; H, 13.1; N, 19.65. Calc. for C$_8$H$_{18}$N$_2$; C, 67.55, H, 12.75; N, 19.7.

EXAMPLE 9

Trans-(±)-N-methyl-N-[2-(methylamino)cyclohexyl]-benxo[b]thiophene-4-acetamide monohydrochloride A solution of benzo[b]thiophene-4-acetic acid (4.65 g, 24 mmol) and carbonyldiimidazole (3.95 g, 24 mmol) in tetrahydrofuran (20 ml) was heated to reflux for 0.5 hours, then cooled to 0° C. and added dropwise over 25 minutes to a stirred solution of trans-(±)-N,N'-dimethylcyclohexane-1,2-diamine (3.0 g, 21 mmol) in tetrahydrofuran (10 ml) at −13° C. The mixture was stirred for a further two hours and allowed to warm to room temperature. The solvent was removed in vacuo to give residue which was dissolved in dichloromethane (100 ml) and washed with aqueous potassium carbonate (100 ml) then water (100 ml). The organic fraction furnished an oily residue which after high pressure liquid chromatography (Waters 500 Prep HPLC silica gel, 80:20:1 ethyl acetatemethanol-triethylamine) gave a light yellow oil (3.3 g); Vmax (liquid file) 3320, 1635 cm$^{-1}$.

Formation of hydrochloride salt: Method L: The oil (3.3 g) was dissolved in diethyl ether (100 ml), filtered through a plug of cotton wool and treated with a solution of hydrogen chloride in diethyl ether until the solution became acidic. The resulting white precipitate was isolated by filtration and washed with diethyl ether. This procedure furnished trans-(±)-N-methyl-N-[2-(methylamino) cyclohexyl]benzo[b]thiophene-4-acetamide monohydrochloride (3.0 g, 40%).

EXAMPLE 10

Trans-(±)-N-(2-[(cyclopropylmethyl)methylamino]-cyclohexyl)-N-methylbenzo[b]thiophene-4-acetamide monohydrochloride A solution of trans-(±)-N-methyl-N-[2-(methylamino)cyclohexyl]benzo[b]thiophene-4-acetamide monohydrochloride (200 mg, 0.57 mmol) in dichloromethane (10 ml) was treated with 10% aqueous potassium carbonate to liberate the parent amine. This oil was dissolved in dichloromethane (1 ml) and triethylamine (0.15 ml, 1.1 mmol) treated with bromomethylcyclopropane (220 mg, 1.6 mmol) and heated to reflux for 26 hours. After standing at room temperature for 70 hours the mixture was poured into 10% aqueous potassium carbonate (10 ml) and extracted with dichloromethane (3×15 ml) to give an oil which after silica gel chromatography (100:1 ethyl acetatetriethyl-amine) furnished trans-(±)-N-(2-[(cyclopropylmethyl)methylamino]cyclohexyl)-N-methylbenzo[b]thiophene-4-acetamide (200 mg, 95%) δ$_H$ (CDCl$_3$) 0.7–0.0 (5H, m); Vmax (liquid film) 3080, 1635 cm$^{-1}$.

The hydrochloride salt of this oil (250 mg) was prepared as described in Method L and recrystallized (dichloromethane-diethyl ether) to give a white solid (200 mg, 73%); m.p. 229°–234° C.

EXAMPLE 11

Trans-(±)-N-methyl-N-(2-[methyl(2-propenyl)amino]-cyclohexyl)benzo[b]thiophene-4-acetamide monohydrochloride A solution of trans-(±)-N-methyl-N-[2-(methylamino)-cyclohexyl]benzo[b]thiophene-4-acetamide monohydrochloride (400 mg, 1.13 mmol) in dichloromethane (10 ml) was treated with aqueous potassium carbonate (30 ml) to liberate the parent amine. This oil was dissolved in ethanol (10 ml), dichloromethane (1 ml) and triethylamine (0.3 ml, 2.2 mmol) and treated with allyl bromide (257 mg, 2.1 mmol). This mixture was stirred in an oil bath at 50°–60° C. for six hours, concentrated in vacuo and partitioned between 10% aqueous potassium carbonate and dichloromethane. The organic fractions furnished an oil which after silica gel chromatography (100:1 ethyl acetate-triethylamine) gave trans-(±)-N-methyl-N-(2-[methyl(2-propenyl)amino]cyclohexyl)benzo[b]thiophene-4-acetamide (270 mg, 67%); δ$_H$ (CDCl$_3$) 6.0–4.3 (3H, m); Vmax (liquid film) 1637 cm$^{-1}$.

015
The hydrochloride salt was prepared as described in Method L and recrystallized (dichloromethanediethyl ether) to give a white solid (170 mg; 57%); m.p. 209°–211.5° C.

EXAMPLE 12

Trans-(±)-N-methyl-2-(1-piperidinyl)cyclohexanamine

A stirred mixture of N-methylazabicyclo [4.1.0]heptane (5.0 ml, 39 mmol), piperidine (3.9 ml, 39 mmol) and ammonium chloride (0.2 g dissolved in 0.4 ml water) was heated to reflux for 5.5 h. Bulb to bulb distillation yielded trans-(±)-N-methyl-2-(1-piperidinyl)cyclohexanamine as a colourless liquid (oven temperature 210°/20 mm) (3.2 g, 42%); $\delta_H$ (CDCl$_3$) 2.34 (3H, s).

EXAMPLE 13

Trans-(±)-N-methyl-N-[2-(1-piperidinyl)cyclohexyl]-benzo[b]thiophene-4-acetamide monohydrochloride A stirred solution of benzo[b]thiophene-4-acetic acid (0.50 g, 2.6 mmol) and carbonyl di-imidazole (0.46 g, 2.8 mmol) in tetrahydrofuran (5 ml) was heated with a solution of trans-(±)-N-methyl-2-(1-piperidinyl)cyclohexanamine (0.46 g, 2.3 mmol) in tetrahydrofuran (2 ml). This mixture was heated to reflux for five minutes, concentrated in vacuo, poured into saturated aqueous sodium bicarbonate (30 ml) and extracted with dichloromethane (2×20 ml) to give an oil which on trituration with diethyl ether gave trans-(±)-N-methyl-N-[2-(1-piperidinyl)cyclohexyl]benzo[b]thiophene-4-acetamide as a crystalline solid (610 mg, 72%); VmaxC=O (liquid film) 1635 cm$^{-1}$.

The hydrochloride salt of this amine (370 mg, 1.0 mmol) was prepared as described in Method L and recrystallized (dichloromethane-diethyl ether) to given a white solid (0.40 g, 98%).

EXAMPLE 14

Trans-(±)-N-methyl-N-(2-(methyl[(tetrahydro-2-fruanyl)methyl]amino)cyclohexyl)benzo[b]thiophene-4-acetamide monohydrochloride A solution of trans-(±)-N-methyl-N-[2-(methylamino)cyclohexyl]benzo[b]thiophene-4-acetamide monohydrochloride (120 mg, 0.34 mmol) in dichloromethane (10 ml) was treated with saturated aqueous sodium bicarbonate to liberate the parent amine. The oil was dissolved in dimethyl formamide and treated with tetrahydrofurfuryl bromide (68 mg, 0.41 mmol) and sodium bicarbonate (43 mg, 0.5 mmol). The resulting mixture was stirred in an oil bath at 95°–110° C. for 20 hours then concentrated in vacuo, poured into saturated aqueous sodium bicarbonate (15 ml) and extracted with dichloromethane (2×15 ml). Silica gel chromatography (70:30:1 ethyl acetate-hexanetriethylamine) furnished trans-(±)-N-methyl-N-(2-(methyl[(tetrahydro-2-furanyl)methyl]amino)cyclohexyl)-benzo[b]thiophene-4-acetamide as a colourless oil (43 mg, 32%); m/e: 400 (M+), 329, 286, 195, 147; t.l.c. analysis of this product (50:50:1 ethyl acetate-hexane-triethylamine, multiple development) indicated that it consisted of two components.

The hydrochloride salt of this amine (42 mg, 0.10 mmol) was prepared as described in Method L to give a white solid (13 mg, 28%).

EXAMPLE 15

2-(4-benzo[b]thiophene)propionic acid n-Butyl lithium (4.0 ml of a 1.6M solution in hexane, 6.4 mmol) was added to a stirred solution of benzo[b]thiophene-4-acetic acid (0.60 g, 3.1 mmol) in tetrahydrofuran (10 ml) and dimethyl sulphoxide (4 ml) with cooling in ice water. After 40 minutes at 0° C. the resulting solution was treated with methyl iodide (190 μl, 3.1 mmol) and stirred at room temperature for 3.3 hours. Concentration in vacuo furnished a red oil which was poured into 5% aqueous sodium hydroxide (50 ml) and washed with diethyl ether (3×30 ml). The aqueous fraction was acidified with concentrated nitric acid and extracted with dichloromethane (3×50 ml) to give a red oil (0.65 g) which after silica gel chromatography (70:30 ethyl acetate-hexane+0.5% acetic acid) gave 2-(4-benzo[b]thiophene)propionic acid as an off-white solid (0.26 g, 38%); $\delta_H$ (CDCl$_3$) 11.4 (1H, s); 8.0–7.0 (5H, m); 4.28 (1H, q, J 7 Hz); 1.62 (3H, d, J 7 Hz).

EXAMPLE 16

Trans-(±)-N-methyl-N-(2-pyrrolidinylcyclohexyl)-4-benzo[b]thiophene-2-propionamide A stirred solution of 2-(4-benzo[b]thiophene)-propionic acid (98 mg, 0.47 mmol) and carbonyl diimidazole (78 mg, 0.48 mmol) in tetrahydrofuran (0.5 ml) was heated to reflux for 0.5 hours then cooled to room temperature and treated with a solution of trans-(±)-N-methyl-2-(1-pyrrolidinyl)-cyclohexanamine (76 mg, 0.42 mmol) in tetrahydrofuran (0.5 ml). This mixture was heated to reflux for 5.5 hour, poured into saturated aqueous sodium bicarbonate (30 ml) and extracted with dichloromethane (2×20 ml) to give an oil which after silica gel chromatography (50:50:1 ethyl acetate-hexanetriethylamine) furnished trans-(±)-N-methyl-N(2-pyrrolidinyl-cyclohexyl)-4-benzo[b]thiophene-2-propionamide (100 mg, 64%); VmaxC=O (liquid film) 1638 cm$^{-1}$; t.l.c. analysis of this produce (50:50:1 ethyl acetate-hexane-triethylamine) indicated that it consisted of two components. The hydrochloride salt of this diastereoisomeric mixture of amines (80 mg, 0.22 mmol) was prepared as described in Method L to give a white solid (70 mg, 78%).

EXAMPLE 17

Trans-(±)-N-(2-[(1,1-dimethyl-2-propenyl)methylamino]cyclohexyl)-N-methyl-benzo[b]-thiophene-4-acetamide monomhydrochloride and trans-(±)-N-methyl-N-(2-methyl(3-methyl-2-butenyl)amino]cyclohexyl)benzo[b]thiophene-4-acetamide monohydrochloride A stirred solution of trans (±)-N-methyl-N-[2-(methylamino)cyclohexyl]benzo[b]thiophene-4-acetamide (330 mg, 1.04 mmol) in dichloromethane (2 ml) was treated with 1-bromo-3-methyl-but-2-ene (140 μl) and sodium bicarbonate (160 mg, 1.9 mmol) and heated to reflux for 1.5 hours. The mixture was poured into saturated aqueous sodium bicarbonate (10 ml) and extracted with dichloromethane (2×10 ml). Silica gel chromatography (70:30:1 ethyl acetate-hexanetriethylamine) furnished an oil (260 mg, 65%); VmaxC=O (liquid film) 1640 cm−1, which was homogeneous by t.l.c analysis (70:30:1 ethyl acetatehexane triethylamine) but analysis by $^1$H n.m.r. indicated the presence of the parent amines of the above two compounds.

The hydrochloride salts were formed as described in Method L and recrystallized (dichloromethane-diethyl ether) to give a white solid (0.27 g, 94%), $^1$H- n.m.r. (CDCl$_3$) integration indicates the presence of trans-(±)-N-(2-[(1,1-dimethyl-2-propenyl)methylamino]-cyclohexyl-N-methyl-benzo[b]thiophene-4-acetamide monohydrochloride and trans-(±)-N-methyl-N-(2-[methyl(3-methyl-2-butenyl)amino]cyclohexyl)benzo[b]thiophene-4-acetamide monohydrochloride in a 5:2 ratio respectively.

EXAMPLE 18

Trans-(±)-N-methyl-N-[2-(1-pyrrolidinyl)cyclohexyl]-benzo[b]thiophene-3-acetamide monohydrochloride By Method A, benzo[b]thiophene-3-acetic acid (384 mg, 2 mmol) was converted to the amide monohydrochloride (716 mg, 91%); VmaxC=0 1645 cm$^{-1}$.

EXAMPLE 19

Trans-(±)-N,2-dimethyl-N-[2-(1-pyrrolidinyl)cyclohexyl]-3-benzofurancetamide monohydrochloride By Method A, 2-methyl-3-benzofuranacetic acid (380 mg, 2 mmol) was converted to the amide monohydrochloride (606 mh, 78%); VmaxC=0 1645 cm$^{-1}$.

EXAMPLE 20

Trans-(±)-N-methyl-N-[2-(1-pyrrolidinyl)cyclohexyl]-1H-indene-3-acetamide monohydrochloride By Method C, 1H-indene-3-acetic acid (174 mg, 1 mmol) was converted to the amide. The crude product was dissolved in methylene chloride (5 ml) and treated with a solution of hydrogen chloride in diethyl ether until the solution became acidic. Diethyl ether was then added until no more precipitate appeared. The product was collected by filtration, washed with diethyl ether and dried in a vacuum at 70° C. overnight, to yield the amide monohydrochloride (80 mg, 21%); VmaxC=0 1640 cm$^{-1}$.

EXAMPLE 21

Trans-(±)-N-methyl-3-phenyl-N-[2-(1-pyrrolidinyl)cyclohexyl]-5-benzofurancetamide monohydrochloride By Method B, 3-phenyl-5-benzofuranacetic acid (252 mg, 1 mmol) was converted to the amide monohydrochloride (363 mg, 80%); VmaxC=0 1640 cm$^{-1}$.

EXAMPLE 22

Trans-(±)-N-methyl-N-[2-(1-pyrrolidinyl)cyclohexyl]-1H-indene-2-acetamide momnohydrochloride By Method C, 1H-indene-2-acetic acid (174 mg, 1 mmol) was converted to the amide. The crude product was dissolved in methylene chloride (3 ml) and treated with a solution of hydrogen chloride in diethyl ether until the solution became acidic. Diethyl ether was then added until no more precipitate appeared. The product was collected by filtration, washed with diethyl ether and dried in vacuum oven at 70° C. overnight, to yield the amide monohydrochloride (110 mg, 29%); VmaxC=0 1645 cm$^{-1}$.

EXAMPLE 23

Trans-(±)-N-methyl-N-[2-(1-pyrrolidinyl)cyclohexyl]-3-(2-thienyl)benzo[b]thiophene-7-acetamide monohydrochloride By Method C, 3-(2-thienyl)benzo[b]thiophene-7-acetic acid (215 mg, 0.78 mmol) was converted to the amide. The crude product was dissolved in methylene chloride (3 ml) and treated with a solution of hydrogen chloride in diethyl ether until the solution became acidic. Diethyl ether was then added until no further precipitate appeared. The product was collected by filtration, washed with diethyl ether, and dried in a vacuum oven at 80° C. overnight, to yield the amide monohydrochloride (200 mg, 54%); VmaxC=0 1635 cm$^{-1}$.

EXAMPLE 24

Trans-(±)-N-methyl-3-phenyl-N-[2-(1-pyrrolidinyl)-cyclohexyl]benzo[b]thiophene-5-acetamide monohydrochloride By Method B, 3-phenylbenzo[b]thiophene-5-acetic acid (268 mg, 1 mmol) was converted to the amide monohydrochloride (329 mg, 70%); VmaxC=0 1645 cm$^{-1}$.

EXAMPLE 25

Trans-(±)-N-methyl-7-propyl-N-[2-(1-pyrrolidinyl)cyclohexyl]benzo[b]thiophene-4-acetamide monohydrochloride By Method B, 7-propylbenzo[b]thiophene-4-acetic acid (234 mg, 1 mmol) was converted to the amide monohydrochloride (423 mg, 97%); VmaxC=0 1645 cm$^{-1}$.

EXAMPLE 26

Trans-(±)-2-(benzo[b]thiophen-3-yloxy)-N-methyl-N-[2-(1-pyrrolidinyl)cyclohexyl]acetamide monohydrochloride By Method D, (benzo[b]thien-3-yloxy)acetic acid (104 mg, 0.5 mmol) was converted to the amide. The crude product was purified by column chromatography on silica, using 1% triethylamine in 1:1 hexane/ethyl acetate as elutant. The resulting solution was evaporated and the residue dissolved in dichloromethane (3 ml). A solution of hydrogen chloride in diethyl ether was added until the solution became acidic, then diethyl ether added until precipitation was complete. The product was collected by filtration, washed with diethyl ether and dried in a vacuum oven at 70° C. overnight to yield the amide monohydrochloride (49 mg, 24%); VmaxC=0 1660 cm$^{-1}$.

EXAMPLE 27

Trans-(±)-N,5-dimethyl-N-[2-(1-pyrrolidinyl)cyclohexyl]benzo[b]thiphene-3-acetamide monohydrochloride By Method B, 5-methylbenzo[b]thiophene-3-acetic acid (206 mg, 1 mmol) was convereted to the amide monohydrochloride (349 mg, 86%); VmaxC=0 1640 cm$^{-1}$.

EXAMPLE 28

Trans-(±)-5-chloro-N-methyl-N-[2-(1-pyrrolidinyl)-cyclohexyl]benzo[b]thiophene-3-acetamide monohydrochloride By Method B, 5-chlorobenzo[b]thiophene-3-acetic acid (226.5 mg, 1 mmol) was converted to the amide monohydrochloride (374 mg, 87%); VmaxC=0 1635 cm$^{-1}$/Please could you replace example 3 in PD 3164-41 with the preferred method.

Trans-(±)-N-methyl-N-[2-(1-pyrrolidinyl)cyclohexyl]-1H-indole-3-acetamide

Indole-3-acetic acid (0.7 g, 4 mmol) was dissolved in tetrahydrofuran and carbonyl di-imidazole (0.7 g) added. The solution was boiled and allowed to stand for five minutes. Trans-(±)-N-methyl-2-(1-pyrrolidinyl)cycloheanamine (0.73 g, 4 mmol) was added.

The solution was refluxed for five minutes, evaporated, and washed with excess saturated sodium bicarbonate solution. The solution was extracted three times with an ether/ethylacetate mixture, the combined extracts washed with water, dried (MgSO4), and evaporated to give the amide as white plates (0.76 g, 56%) mp 189°–190.5° C.; VmaxC=0 1605 cm$^{-1}$.

EXAMPLE 29

Trans-(±)-N-methyl-N-[2-(1-pyrrolidinyl)cyclohexyl]N$^\omega$-oxide-benzo[b]thiophene-4-acetamide A solution of trans-(±)-N-methyl-N-[2-(1-pyrrolidinyl)-cyclohexyl]benzo[b]thiophene-4-acetamide (0.41 g) in dichloromethane (10 ml) was treated with m-chloroperoxybenzoic acid (100 mg) and stirred at 0° C. After 50 minutes more m-chloroperoxybenzoic acid (153 mg) was added and after a total of 110 minutes the mixture was poured into saturated aqueous sodium bicarbonate (20 ml) and extracted with dichloromethane (2×10 ml) to give a white solid. Recrystallization (dichloromethane-diethyl ether) furnished pure trans-(>)-N-methyl-N-[2-(1-pyrrolidinyl)cyclohexyl]-N1-oxide-benzo[b]thiphene-4-acetamide (0.31 g, 72%), mp 149°–151.5° C.

EXAMPLE 30

Trans-(±)-N-methyl-N-[2-[methyl(2-propynyl)amino]-cyclohexyl]benzo[b]thiophene-4-acetamide monohydrochloride A solution of trans-(±)-N-methyl-N-[(methylamino)-cyclohexyl]benzo[b]thiophene-4-acetamide monohydrochloride (450 mg) in dichloromethane (20 ml) was treated with saturated aqueous sodium bicarbonate to liberate the parent amine. This oil was dissolved in dichloromethane (2.5 ml) and treated with propargyl bromide (250 μl of an 80% solution in toluene) and triethylamine (0.20 ml). After 17 hours at room temperature, potassium carbonate (200 mg) and more dichloromethane (18 ml) were added. After 1.5 days the mixture was decanted and the supernatant was treated with propargyl bromide (150 μl of an 80% solution in toluene) at room temperature. After a further 12 hours this solution was poured into saturated aqueous sodium bicarbonate (20 ml) and extracted with dichloromethane (2×20 ml). Silica gel chromatography (4:1 ethyl acetate-methanol containing 1% triethylamine) furnished trans-(±)-N-methyl-N-[2[methyl(2-propynyl-)amino]cyclohexyl]benxo[b]thiophene-4-acetamide (220 mg, 49%). Vmax liquid file 3300, 3225, 2110, 1630 cm$^{-1}$. The hydrochloride salt of this compound (220 mg) was prepared as described in Method L to give a white solid (230 mg, 93%).

I claim:
1. A compound having the structural formula

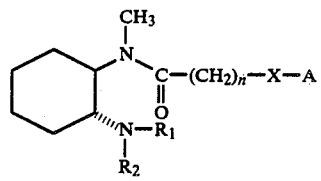

where $R_1$ is methyl and $R_2$ is hydrogen, alkyl of from one to six carbon atoms,

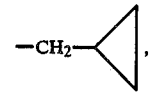

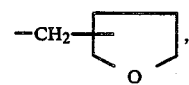

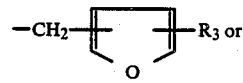

—CH$_2$CH=CR$_3$R$_4$ where $R_3$ and $R_4$ are independently hydrogen or methyl; or where $R_1$ and $R_2$ taken together with the nitrogen atom to which they are attached form a pyrrolidinyl ring;
where n is an integer of from zero to six;
X is
oxygen,
sulfur,
—CHR$_5$ where $R_5$ is
hydrogen,
alkyl of from one to six carbon atoms,
phenyl,
phenyl substituted with
fluorine,
chlorine,
alkyl of from one to six carbon atoms,
alkoxy of from one to six carbon atoms,
nitro,
trifluoromethyl,
2- or 3-thienyl, or
2- or 3-thienyl substituted with
alkyl of from one to six carbon atoms,
alkoxy of from one to six carbon atoms; or
NR$_6$ where $R_6$ is
hydrogen or
alkyl of from one to six carbon atoms;
where A is

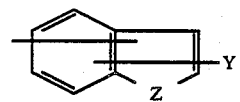

Y is
hydrogen,
fluorine,
chlorine,
alkyl of from one to six carbon atoms,
phenyl;
phenyl substituted with
fluorine, chlorine,
alkyl of from one to six carbon atoms,
alkoxy of from one to six carbon atoms,
nitro,
trifluoromethyl,
2- or 3-thienyl; or
2- or 3-thienyl substituted with
  alkyl of from one to six carbon atoms,
  alkoxy of from one to six carbon atoms; and
Z is oxygen
or a pharmaceutically acceptable acid addition salt thereof.

2. A compound in accordance with claim 1 wherein n is an integer of from zero to two; and the pharmaceutically acceptable acid addition salts thereof.

3. A comound in accordance with claim 1 selected from the group consisting of:
trans-N-2,-dimethyl-N-[2-(1-pyrrolidinyl)cyclohexyl]-3-benzofuranacetamide;
trans-N-methyl-phenyl-N-[2-(1-pyrrolidinyl)cyclohexyl]-5-benzofuranacetamide;
and the pharmaceutically acceptable acid addition salts thereof.

4. A pharmaceutical composition useful for alleviating pain in a mammal, said composition comprising an effective amount of a compound in accordance with claim 1 in combination with a pharmaceutically acceptable carrier.

5. A method of alleviating pain in a mammal in need of such treatment, said method comprising administering to said mammal a pharmaceutical composition in accordance with claim 4 in unit dosage form.

* * * * *